United States Patent [19]

Markowski

[11] Patent Number: 5,005,424
[45] Date of Patent: Apr. 9, 1991

[54] MACHINE AND METHOD FOR UNIAXIAL MECHANICAL MATERIAL TESTING

[75] Inventor: Winfried Markowski, Berlin, Fed. Rep. of Germany

[73] Assignee: Bundesanstalt für Materialforschung und -prüfung (BAM), Berlin, Fed. Rep. of Germany

[21] Appl. No.: 505,275

[22] Filed: Apr. 6, 1990

[30] Foreign Application Priority Data

Apr. 10, 1989 [DE] Fed. Rep. of Germany ....... 3912075

[51] Int. Cl.$^5$ .............................................. G01N 3/08
[52] U.S. Cl. ........................................ 73/834; 73/837
[58] Field of Search .................. 73/826, 831, 834, 837, 73/818, 825, 847, 821, 848, 788, 789, 834

[56] References Cited

U.S. PATENT DOCUMENTS

3,135,106 6/1964 Lazan .................................. 73/794 X

*Primary Examiner*—Jerry W. Myracle
*Attorney, Agent, or Firm*—Spencer & Frank

[57] ABSTRACT

Testing machine for the mechanical testing of material samples comprising a first and a second force engagement device, a first and a second sample engagement device, a first force measuring device which is positioned between the first sample engagement device on the one hand and the force by-pass device together with the first force engagement device on the other hand, an actuator to create the force to be applied, a force by-pass device which is connected to the first force engagement device and which tranfers an applied prestress force acting on one of the force engagement devices to the other while by-passing the sample positioned between the two sample engagement devices, whereby the force by-pass device is stiff, the second sample engagement device is, by way of a length adjustment device, slidably mounted in the direction of the application of force relative to the end of the force by-pass device which is not connected to a force engagement device and whereby the length adjustment device is connected to the second force engagement device and the second force engagement device is connected to the actuator which creates the force to be applied whereby a device which defines a prestress force to be applied during testing is connected to the actuator.

23 Claims, 6 Drawing Sheets

MACHINE AND METHOD FOR UNIAXIAL MECHANICAL MATERIAL TESTING

CROSS REFERENCE TO RELATED APPLICATION

This application claims the priority of Federal Republic of Germany Application No. P 39 12 075.9 filed Apr. 10th, 1989, which is incorporated herein by reference.

BACKGROUND OF THE INVENTION

This invention relates to a testing machine and a method for mechanically testing material samples.

A known testing machine is described in the Handbuch der Werkstoffprüfung (Handbook for material testing) published by E. Siebel and L. Ludwig, Springerverlag 1985, Vol. 1, pages 15-17 and 54-55 which determines the relationship between loading and deformation or tension and extension of a material sample. This means that a testing machine which acts as a source of displacement or deformation has to be used which effects a defined deformation as an independent parameter and also measures the thereby resulting forces as a dependent parameter. The testing procedure must not become unstable and go out of control when the resistance to deformation of the sample decreases, in particular when the resistance to deformation changes suddenly.

It is further known from the journal "Materialprüfung" (Material Testing), year 12 (1970), Nr.1, pages 1-6 that to fulfil these requirements testing machines are used which have control devices for regulated deformation during testing. In addition it is known from the "Technische Mitteilungen der Krupp Forschungsberichte" (Technical Information from the Krupp Research Reports), Volume 24, 1966, H. 3, pages 79-88, to introduce an elastic by-pass to the sample in order to increase the effective spring constant of the testing machine. With the regulated deformation testing machine the actuator of the testing machine is operated by applying closed-loop control, so that either the displacement of the actuator or the machine traverse or the extension monitored in the sample by an extension transducer is compared with the predetermined theoretical value and the actual force applied by the testing machine for the displacement or the extension is measured.

Due to this the regulated deformation testing machine acts only as an indirect or an imitative source of displacement and deformation, which also means that only an indirect presetting of deformation is possible. The testing machine with the sum of its tractilities including that of the actuator acts in principal as a colinear spring in relation to the sample and therefore acts as a direct mechanical force at least in the case of small paths of deformation.

This leads to the following disadvantages:

During small spontaneous variations in the tractility of the sample during testing as occurs when passing through the yield limit of a steel sample or when microcracking occurs in concrete samples, the sample is further deformed disadvantageously in the direction of loading as the testing machine springs back in elastic compensation. This occurs spontaneouosly and independently of the testing machine actuator and is therefore not controllable. The sudden occurence of such phenomena often sets off a number of similar microprocesses in the sample structure untill an equilibrium between the spring loads of the sample and the testing machine is again reached. This means that the structure of the sample is damaged unintentionally with a scattered falsifying influence on the results of the test.

The known testing machines cannot in principal prevent the already described compensation processes between the sample and the testing machines from taking place due to the indirect predetermination of deformation. In particular, the control function of the known testing machine in itself produces faulty test results due to the following: The control circuit can only react to the deviations from the preset value after they have occured, i.e. only after such a sudden compensation process between sample and testing machine has taken place and can only then correct the deformational deviation with the actuator as adjustment.

This deformation adjustment carried out by the control device leads to sizeable errors in the test results because the force patterns during an increase or a decrease of deformation in the plastic region are quite different from one another. When passing through the yield limit region of a steel sample for example, the lower yield stress limit is grossly incorrect, as after the extension leap has occured and the test machine has sprung back in consequence, this extension value is then deducted by the actuator to correct the test extension, which leads to the force applied decreasing much more steeply and running parallel to the elastic curve of the sample unlike during extension when the force diagram is relatively flat. This means that the value for the lower yield stress limit is far too low.

By setting a constant actuation or traverse speed of the testing machine it is not possible to obtain a constant deformation speed of the sample since the tractility in the colinear series machine-sample changes with a decreasing resistance to deformation of the sample and with that their individual contributions to deformation also change. In the plastic region and subjected to an approximately constant applied force, the sample receives all of the actuator motion as deformation and is then additionally deformed by the springing back of the testing machine when the loading is decreased. In this way the deformational speed of the sample, as for example during a tensile test, increases in an uncontrolled fashion up until ultimate failure even though a constant actuator speed is applied.

By positioning the sample and the testing machine in series the forces acting on the testing machine change automatically with the test force applied, which in the case of never to be ruled out unsymmetrical installation joints and an unsymmetrical construction of the testing machine lead to unsymmetrical load-dependent deformations, i.e. to a slanting position of the sample. It also automatically leads to a total unloading and to the connected springing back of the testing machine which occurs suddenly, in particular when testing brittle materials. Because of this, with time, the connections and the joints of the testing machine loosen and show signs of wear which can lead to faults, such as load-dependent slanted positions, which give rise to test errors and bad reproducibility, superimposed bending moments and faults in the actuator system.

The known testing machines are complicated and expensive. One tried to minimise the described disadvantages of these machines by using the stiffest machine construction possible, fast and sensitively reacting actuation devices and complicated control devices. The disadvantages could nevertheless not be prevented fully due to their inherent nature.

The known non-adjustable, elastic force by-pass devices as described in DE-PS 35 22 453 C2 and in the "Technische Mitteilungen der Krupp Forschungsberichte", 1966, H3 still have the mutual disadvantage that a force can only be applied to them if a force is also applied to the sample and at the same time can only enable a small deformation of the sample to take place due to the alteration of the force applied to the testing machine in the region of elastic deformation of the springs positioned parallel to the sample. These embodiments do not possess the crucial characteristic of an adjustable source of movement to enable the predetermination of a defined deformation force independent of the force applied and are not able to eliminate the influence of the deformation of the testing machine as this influence is inherent to this type of testing machine.

SUMMARY OF THE INVENTION

It is an object of the invention to provide a testing machine which acts as a direct source of displacement or deformation and also to provide a method of testing with a direct predetermined deformation which in a simple manner avoids the described disadvantageous influence of the tractibility of the testing machine and the closed-loop control of the actuator.

The advantages of the invention are, in particular, that the testing machine comprises a rigid force by-pass device in connection with a length adjustment device which is attached to the first force engagement device. The force by-pass device transfers an applied prestress force acting on one of the force engagement device to the other whilst by-passing the sample positioned between the two sample engagement devices. A first force measuring device is positioned between the first sample engagement device on the one hand and the force by-pass device together with the first force engagement device on the other hand. The second sample engagement device is mounted on and connected with a length adjustment device at the end of the force by-pass device which is not connected to a force engagement device in the direction of the application of force. In this region the length adjustment device is also connected to the second force engagement device. The second force engagement device is, in addition, connected to an actuator which creates the force to be applied. The actuator comprises a device which defines a prestress force to be applied during testing.

This arrangement provides an adjustable source of displacement in the form of the length adjustment device to predetermine a defined path of deformation. The set constant prestress force to be applied to the testing machine eliminates the influence of the testing machine deformation. The first force measuring device only measures the test force acting directly on the sample.

In particular the following are advantageous features of the invention:

A second force measuring device is attached to one of the force engagement devices as part of the device which predetermines a prestress force to be applied. In this way the prestress force applied can be monitored. The length adjustment device consists of a spindle and a spindle nut which bears on the force by-pass device. A setting motor which is connected with the spindle nut is attached to the force by-pass device which is constructed as a rectangular frame, pot or cage. The spindle nut and the setting motor are situated inside the frame, pot or cage of the force by-pass device for tensile testing and outside the frame, pot or cage of the load by-pass device for compressional testing. This solution is particularly advantageous due to its simplicity.

In a further advantageous embodiment of the invention the length adjustment device is in the form of a hydraulic system which transfers the applied force into the force by-pass device. Adjustment whilst the force is being applied is accomplished by a dosed change in the volume of the liquid in the cylinder with the control valve. In this way the setting of predetermined deformation values is possible even at high speeds without having to utilise a special actuator aggregate. By utilising a low pressure accumulator to hold the released fluid the piston of the cylinder of the length adjustment device can be reset automatically when unloading the testing machine. A further advantageous embodiment which enables the length adjustment device to be reset against the test force applied and thereby allowing for a bulging deformation of the sample is accomplished by a simple connection with a cylinder whose piston is displaced with a threaded spindle which can be adjusted in a defined manner.

In order to be able to adapt the known testing machines to the new method the force engagement devices are of a cylindrical or rectangular cross-section which can be fixed in the sample engagement devices of the known testing machines. In this case the sample engagement devices act a force engagement surface areas.

According to a further advantageous feature the construction of the testing machine is thus that the sample can be subjected to time-dependent deformations so that the testing machine can be implemented for a number of different tests.

In a further advantageous embodiment the testing machine comprises a further loading system which acts parallel to the force by-pass device and is controlled dependent on the signal from the force measuring device in such a way that an additional force equivalent to that of the test force is applied to the force by-pass device. In this way the force applied and therefore the deformation of the force by-pass device remains constant during testing so that these disturbing influences on the test process no longer occur. In this way the force by-pass device is of an even greater rigidity.

The following test method has proven to be particularly advantageous:

(a) The testing machine is prestressed using the force by-pass device and by reading the second force measuring device, by applying a force which is either greater than the maximum required test force to be applied to the sample or equivalent to a force which is not to be exceeded during testing. In this way the influence of the tractility of the testing machine is completely eliminated as the prestressing of the testing machine remains constant during the duration of testing.

(b) A defined direct deformation of the sample is possible due to a controlled adjustment of the length adjustment device in the test force axis in the direction of yield in relation to the prestressing. The force which is applied is increasingly transferred from the force by-pass device to the sample and the first force measuring device in accordance with the change in the resistance to deformation of the sample. The actuator keeps the total applied force constant and automatically resets the adjustment distance of the length adjustment device which defines the deformation path of the sample and thus provides the deformational energy required.

(c) As the resistance to deformation of the sample decreases the force applied is automatically increasingly transferred to the force by-pass device until the total force acts on the force by-pass device at ultimate failure of the sample. During all of this the total force applied by the actuator remains unchanged.

(d) The testing machine is then unloaded after the test has finally been concluded.

The advantages of the invention are, in particular, that the testing machine acts relative to the sample as a direct source of displacement, i.e. as an energy source with a defined displacement which allows for a method of testing with direct set deformation and a force-limit which can be set in which the tractability of the testing machine no longer influences the test. This in turn leads to the following advantages:

Spontaneous variations in the tractility of the sample, as occurs for example when passing through the yield limit of steel, do not lead to a deformational balance but only to a change in the distribution of the force applied between sample and force by-pass device whilst the force applied by the actuator remains unchanged. In this way the testing machine also no longer springs back in elastic compensation and the structure of the sample is no longer damaged so that the results are not falsely influenced by this phenomena any longer. The loading pattern can now be correctly recorded even if spontaneous variations in the tractility of the sample occur.

Because the actuator of the testing machine no longer controls the deformation the falsifying influence caused by controlling the deformations after the changes have ocurred, as happened during spontaneous variations in the tractility of the sample, i.e. at the yield limit, are now avoided.

Predetermined speeds of deformation are set for the sample directly, and are not dependent on changes in the resistance to deformation of the sample as balancing deformational processes, and, in turn, differing deformational speed distributions between the sample and the testing machine no longer occur. Furthermore the deformational speed can be varied over a very wide range without much difficulty depending on the type of adjustment device used for the setting of the deformational values. Sudden deformations are possible using a hydraulic adjustment device with a sufficiently large valve cross-section and a soft spring in the actuator.

The testing machine is constantly loaded during the entire test since only the distribution of the applied force between the sample and the force by-pass device changes. In this way, all of the changes in the testing machine deformation and its symmetry which are dependent on the test force applied no longer take place, which means that all of the resulting influences on the sample such as bending for example also no longer occur. Similarly, the sudden unloading with ultimate failure and its damaging effect on the testing machine no longer takes place as the force which no longer acts on the sample is simply transferred and is again carried by the force by-pass device and the testing machine can be unloaded in a undamaging manner after the test has been finally concluded.

The testing machine itself no longer needs to fulfil certain requirements regarding rigidity, actuation and quality of control so that the machine is less complicated.

The testing machine can also be designed for moment loading, i.e. for carrying out torsional testing on the sample, since a moment load is simply a force applied with a lever arm. The same advantages can be reached with the arrangement of the testing machine for torsional deformation with time-dependent deformations as are reached for compressional or tensional testing of the sample.

The first and second force engagement devices are in the form of moment engagement devices, the first and second force measuring devices are in the form of moment measuring devices, the actuator to create the force to be applied is in the form of an actuator for moments, the force by-pass device is in the form of a moment by-pass device and the length adjustment device is in the form of an angle adjustment device. The second sample engagement device is rotatably mounted in the direction of rotation of the acting moment via the angle adjustment device on the end of moment by-pass device which is not connected with the moment engagement device.

The arrangement of the testing machine according to this embodiment advantageously provides an adjustable source of displacement in the form of a rotational device which can define set angles of deformation. The testing machine in this embodiment of the invention also acts as a direct source of displacement, i.e. as a source of energy with a defined displacement, and enables a method of testing with direct set deformation and a moment-limit which can be set. With this embodiment of the testing machine its tractility also does not influence the torsional test.

DETAILED DESCRIPTION OF THE INVENTION

Figure 1:
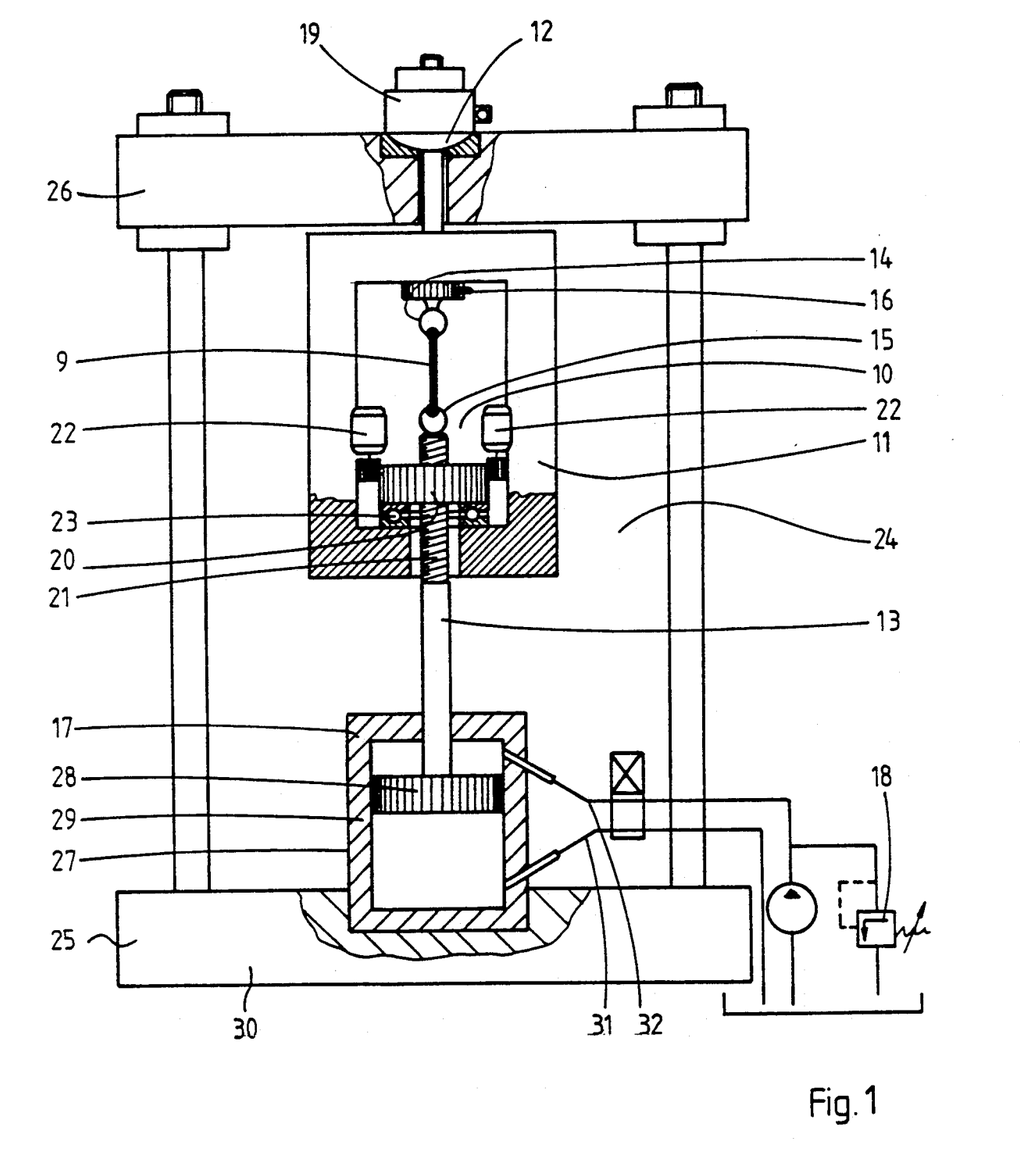
FIG. 1 is a front view of a first embodiment of a testing machine according to this invention.

A hydraulic tensile testing machine for material samples 9 is shown in FIG. 1 as a first embodiment of a testing machine according to the invention. With this machine the force applied by the length adjustment device 10 is distributed to the force by-pass device 11, which is in the form of a rectangular frame, and to the sample. The testing machine comprises first and second force engagement devices 12 and 13, first and second sample engagement devices 14 and 15, a first force measuring device 16 and an actuator 17 to create the force to be applied. The first force engagement device 12 is mounted on the force by-pass device 11. The force by-pass device 11 initially transfers the prestress force acting on one of the force engagement devices 12 or 13 to the other force engagement device 13 or 12 whilst by-passing the sample engaged in the sample engagement devices 14 and 15. The first force measuring device 16 is situated between the first sample engagement device 14 on the one hand and the force by-pass device 11 together with the first force engagement device 12 on the other hand. The second sample engagement device 15 is mounted on and connected with a length adjustment device 10 at the end of the force by-pass device 11 which is not connected to a force engagement device 12 or 13 in the direction in which the force is applied. In this region the length adjustment device 10 is also connected to the second force engagement device 13. The second force engagement device 13 is in addition connected to an actuator 17 for creating the force to be applied. The actuator 17 comprises a device 18 which defines a prestress force during testing and preferably also comprises a spring which can be biased. A second force measuring device 19 is attached to the first force engagement device 12 as part of the device 18 which holds the prestress force at a constant value. In this way the prestress force can be controlled. The length adjustment device 10 consists of a spindle 21 and a spindle nut 20 which bears on the force by-pass device 11. Two setting motors 22 which are connected with the spindle nut 20 are attached to the force by-pass device 11. The spindle nut 20 is situated inside the frame of the force by-pass device 11 on an axial ball bearing 23. The embodiment 24 is situated in a testing machine casing 25. The force engagement device 12 is mounted in a ball socket in a cross-beam 26. The actuation system 17 comprises an hydraulic system 27 with a piston 28 and a cylinder 29 and is connected to the testing machine table 30. The inlet and outflow of hydraulic liquid through hydraulic lines 31 and 32 is controlled by the device 18 which predetermines and holds the prestress force at a constant value.

This embodiment provides an adjustable source of displacement in the form of the length adjustment device 10 to predetermine a defined path of deformation. The set constant prestress force applied to the testing machine eliminates the influence of the testing machine deformation. The first force measuring device 16 only measures the test force acting directly on the sample 9.

A tensile test is carried out by at first setting the length adjustment device 10 downwards so that the actuator 17 is only applying a force to the force by-pass device 11. The material sample 9 is at this stage still load-free. The force created by the actuator 17 of the testing machine is set at a value which is with certainty greater than the maximum expected test force to be applied to the sample 9 to be held constant by reading the second force measuring device 19. By resetting the spindle nut 20 with the setting motor 22 the spindle 21 is, together with the second sample engagement device 15 connected with it, displaced by a predetermined amount, following the tensile force in a downward direction and the sample extends. The force acting on the force by-pass device 11 is lessened by the amount which has been redirected and is now applied to the sample 9. The test force is measured by the first force measuring device 16. The necessary deformational work is carried out by the actuator 17 whose piston 28 displaces itself by the distance set back by the spindle 21 whilst applying the unchanged total force. With decreasing resistance to deformation and eventually at the ultimate failure of the sample 9 the force is again totally applied to the force by-pass device 11. The total force measured by the second force measuring device 19 remains unchanged. This total force is only slowly reduced after the test has been finally concluded.

In general the method of testing is characterized by the following steps:

(a) the testing machine is prestressed using the force by-pass device and by reading the second force measuring device by applying a force which is either greater than the maximum required test force to be applied to the sample or equivalent to an applied force which is not to be exceeded during testing so that the influence of the tractility of the testing machine is completely eliminated since the prestressing of the testing machine remains constant during the duration of testing, (b) a defined direct deformation of the sample is possible due to a controlled adjustment of the length adjustment device in the test force axis in the direction of yield in relation to the prestressing whereby the force which is applied is increasingly transferred from the force by-pass device to the sample and the first force measuring device in accordance with the change in the resistance to deformation of the sample whilst the actuator keeps the total applied force constant and automatically resets the adjustment distance of the length adjustment device which defines the deformation path of the sample and thus provides the deformational energy required, (c) as the resistance to deformation of the sample decreases the force applied is automatically increasingly transferred to the force by-pass device until the total force acts on the force by-pass device at ultimate failure of the sample whereby during all of this time the total force applied by the actuator remains unchanged, (d) the testing machine is then unloaded after the test has finally been concluded.

Figure 2:
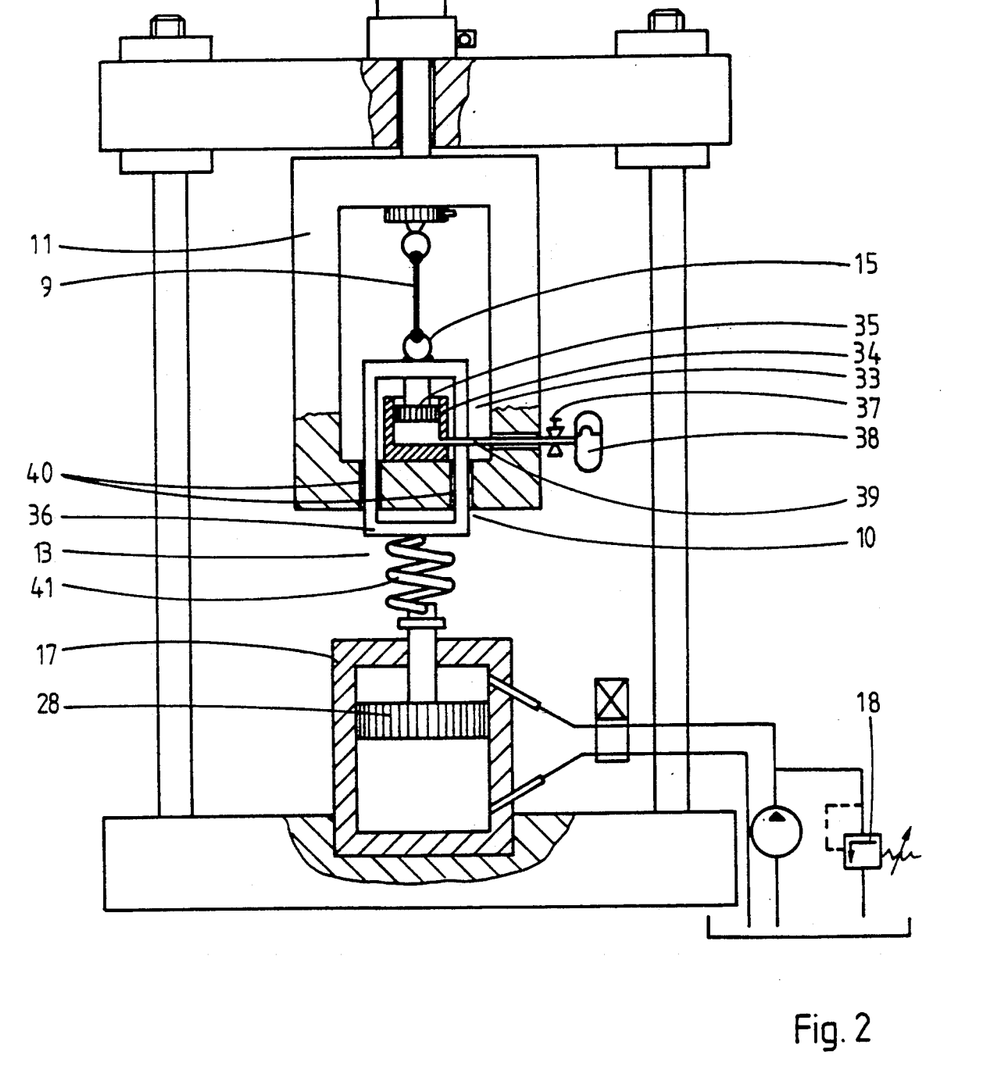
FIG. 2 is a front view of a second embodiment of a testing machine according to the invention.

A second embodiment according to the invention is shown in FIG. 2. The testing machine is essentially the same as the embodiment described in FIG. 1. Only the length adjustment device 10 is different in form. The length adjustment device 10 is in the form of a hydraulic system 33 comprising a hydraulic cylinder 34 and a piston 35. The length adjustment device 10 is connected to the second force engagement device 13 by way of a surrounding frame 36. A control valve 37 is connected with an attached low pressure storage device or accumulator 38 to the hydraulic cylinder 34 by way of lines 39 in the hydraulic system. The force by-pass device 11 comprises a recess 40 for the frame 36. A spring 41 is used to connect the second force engagement device 13 with the actuator 17.

With the testing machine the test force applied is redirected from the force by-pass device 11 to the sample 9 using a hydraulic length adjustment device 10 which can be set. At the start of a tensile test the cylinder 34 of the hydraulic system 33 of the length adjustment device 10 is full of liquid. The position of the second sample engagement device 15 is predetermined in such a manner that no force is acting on the sample 9 during the time when a prestress force is being applied by the testing machine to force load by-pass device 11 with the liquid trapped in the cylinder 34. By letting a certain predetermined amount of liquid out of the cylinder 34 of the length adjustment device 10 through the valve 37 both the position of the second sample engagement device 15 and the extension of the sample 9 are altered by a defined amount. The volume of liquid let off is collected in the low pressure storage device or accumulator 38. The deformational work required is supplied by the actuator 17. The device 18 to keep the prestress force applied constant is equivalent to the device described in FIG. 1. After the testing machine has been unloaded, on conclusion of the test, the liquid flows, due to the minimally higher pressure, from the low pressure storage device or accumulator 38 back into the cylinder 34 of the length adjustment device 10 and brings the piston 35 back into its starting position. The spring 41 is situated between the actuator 17 and the force engagement device 13 so that in the case of sudden deformations of the sample 9 the spring 41 can act as a ready source of a certain amount of deformational energy which is needed when the actuator 17 is speeding up.

Figure 3:
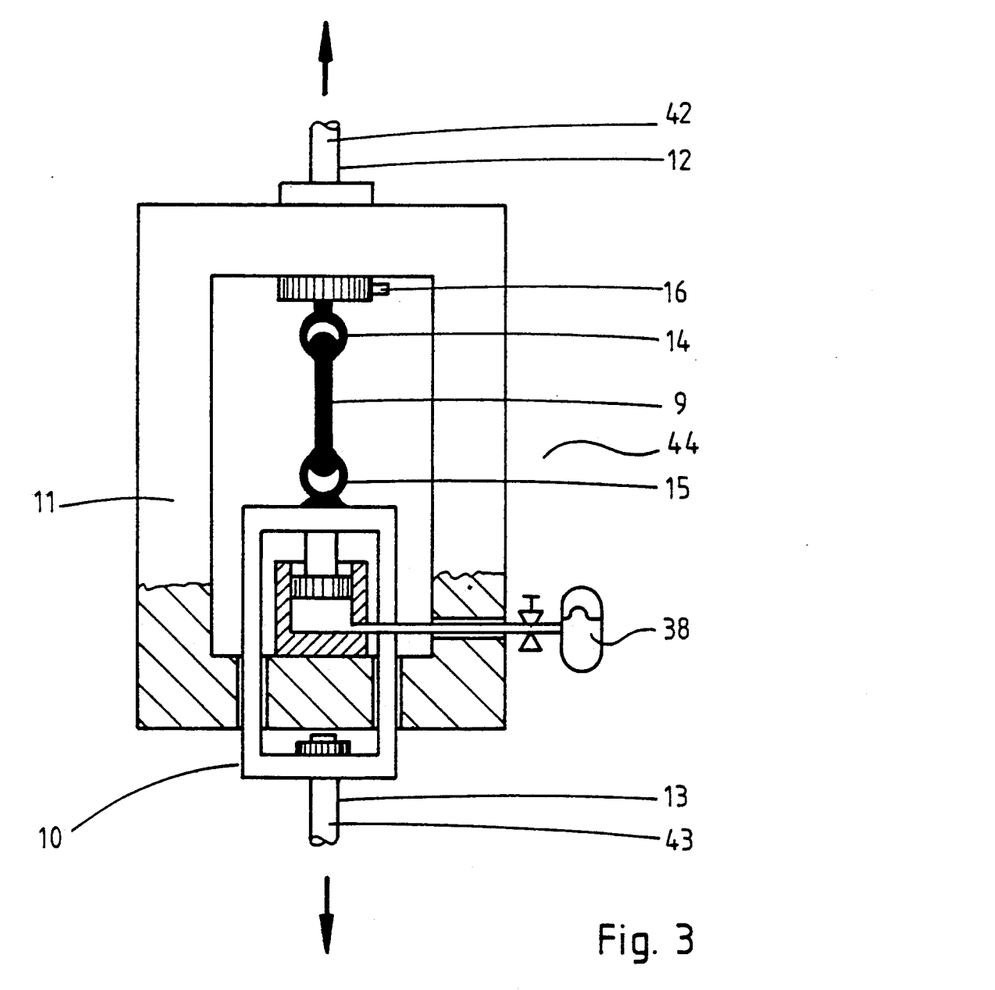
FIG. 3 is a front view of a third embodiment of a testing machine according to this invention.

The third embodiment of the invention is shown in FIG. 3. It is essentially equivalent to the second embodiment described in FIG. 2. The shown embodiment 44 forms an hydraulically resetable independent unit. It comprises a force by-pass device 11, a hydraulic length adjustment device 10 with a low-pressure storage device 38, a first force measurement device 16 and the sample engagement devices 14 and 15 for the sample 9. This independent embodiment 44 can be inserted in the known tensile testing machines and is to be used for their adaptation. In this embodiment the force engagement devices 12 and 13 have a cylindrical cross-section and can be fixed between the sample engagement devices 14 and 15 of the known testing machines. The sample engagement devices 14 and 15 are held by the force engagement areas 42 and 43.

Figure 4:
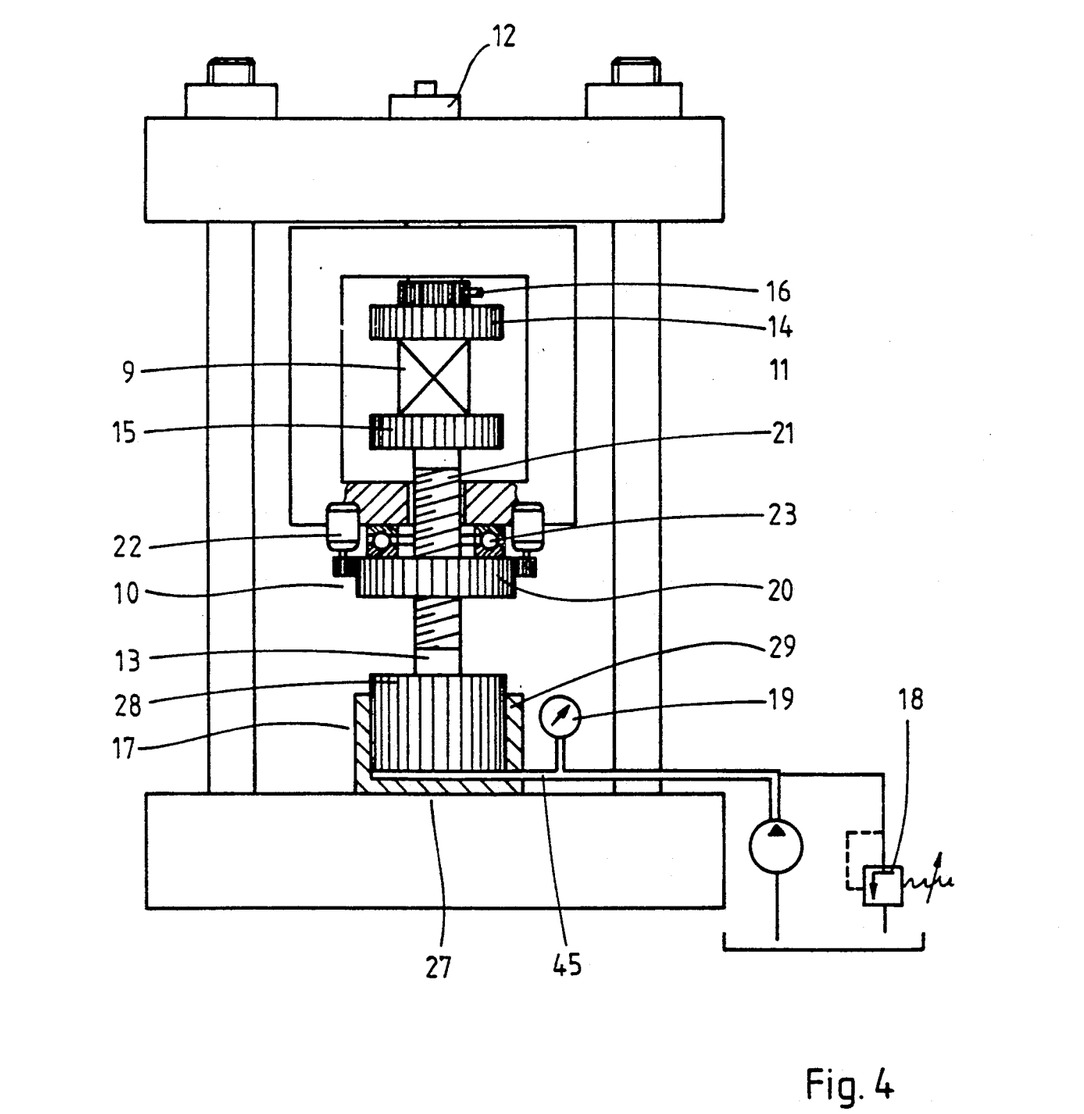
FIG. 4 is a front view of a fourth embodiment of a testing machine according to the invention.

A fourth embodiment of the invention is shown in FIG. 4. This embodiment is a variation of the first embodiment as described in FIG. 1. The setting motors 22, the spindle nut 20 and the ball joint bearing 23 are situated on the outer side of the frame-like, rectangular force by-pass device 11 as this embodiment is used for compressive testing. In addition the second force measuring system 19 is situated in a hydraulic inlet line 45. The actuator 17 comprises a hydraulic system 27, but utilises a piston acting in one direction only. The hydraulic piston 28, cylinder 29, spindle 21, spindle nut 20, force engagement devices 12 and 13 and the sample engagement devices 14 and 15 are greater in size as is required for compressive testing.

A compressive test is carried out by at first only applying a prestress force to the force by-pass device 11 using the length adjustment device 10 which is monitored by the second force measuring device 19 and is greater than the maximum expected test force to be applied to the sample. The sample 9 is then compressed in a defined manner by adjusting the position of the length adjustment device 10 and in which the actuator pushes up by the set compression path and thus carries out the deformational work. The resulting resistance force to deformation in the sample 9 is monitored by the first force measuring device 16 and is the same as the amount by which the force acting on the force by-pass device 11 has lessened due to the redistribution of forces acting at the length adjustment device 10. During this time the total force applied to the testing machine remains constant. The testing machine is only unloaded after the test has finally been concluded.

Figure 5:
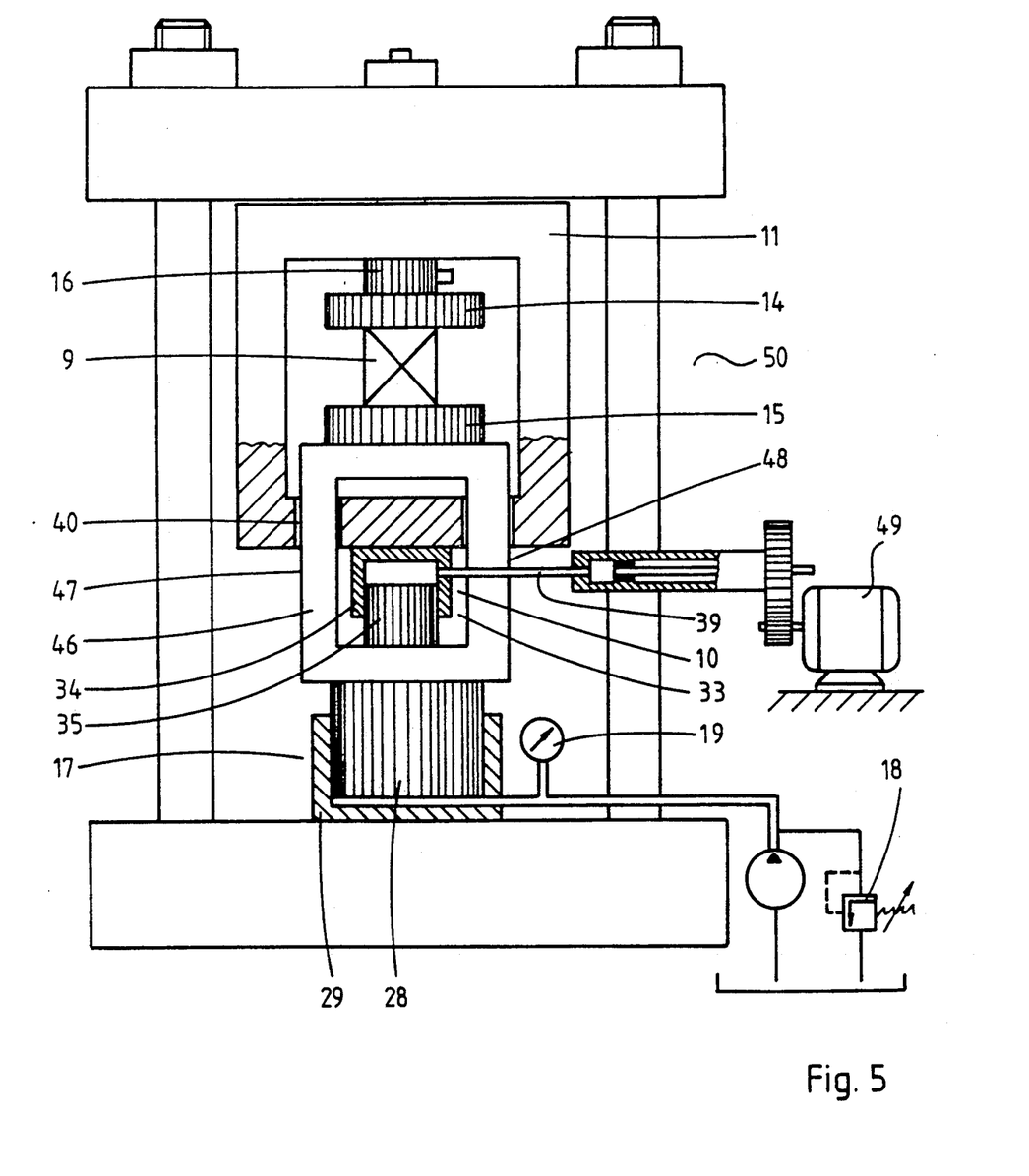
FIG. 5 is a front view of a fifth embodiment of a testing machine according to this invention.

A fifth embodiment of the invention is shown in FIG. 5. This embodiment is a variation of the fourth embodiment shown in FIG. 4. The length adjustment device 10 is in the form of a hydraulic system 33. The piston 28 of the actuator 17 is equivalent to the second force engagement device 13. A rectangular frame 46 is situated on the piston 28 and surrounds the hydraulic cylinder 34 and the hydraulic piston 35 of the length adjustment device 10. The frame 46 with its two side guides 47 and 48 runs through the bores 40 in the force by-pass device 11 into the inside of the frame-like force by-pass device 11. Inside the force by-pass device 11 the frame 46 is connected with the second sample engagement device 15. The hydraulic cylinder 34 of the length adjustment device 10 is connected to a piston-type spindle pump 49 via a line 39. Otherwise the embodiment 50 is the same as the fourth embodiment as shown in FIG. 4.

This embodiment of the invention is especially suitable to be used as a compressive testing machine in which the predetermination of the deformation values for the sample 9 and the related force distribution are carried out by the length adjustment device 10. The length adjustment device 10 at first transfers the force of the actuator 17 via the hydraulic liquid to the force by-pass device 11. By letting the liquid out in a controlled manner the position of the second sample engagement device 15 is altered and the sample 9 is thereby compressed. The force applied is distributed onto the sample 9 and the force by-pass device 11, i.e. the force by-pass device 11 is unloaded by the amount of force which acts on the sample 9. The force acting on the sample 9 is monitored and measured by the first force measuring device 16. The testing machine, to which a constant force is applied throughout the test which is greater than the maximum test force to be applied, is unloaded after the test has been finally concluded. The liquid volume in the cylinder 34 of the length adjustment device 10 is altered by the piston-type spindle pump 49.

In the same way as already described for the above embodiments for testing machines and methods relating to the time-dependent deformation of material samples in tensile and compressive directions, the testing machine can also be used for torsional deformations using the same basic principals of the invention. The material sample is subjected to a moment. The advantages obtained by the testing machine during tensile and compressive testing remain. The first and second force engagement devices 12 and 13 form a moment engagement device, the first and second force measuring devices 16 and 19 are in the form of moment measuring devices, the actuator to create the force to be applied is in the form of an actuator for moments, the force by-pass device 11 is in the form of a moment by-pass device and the length adjustment device 10 is in the form of an angle adjustment device. Furthermore the second sample engagement device 15 is rotatably mounted in the direction of rotation of the acting moment via the angle adjustment device on the end of the moment by-pass device which is not connected with the moment engagement device.

With this embodiment the testing machine also acts in relation to the sample as a direct source of displacement, i.e as an energy source with a defined displacement which allows for a method of testing with direct set deformation and a moment-limit which can be set. The tractility of the testing machine also does not influence the torsional testing with this embodiment.

Figure 6:
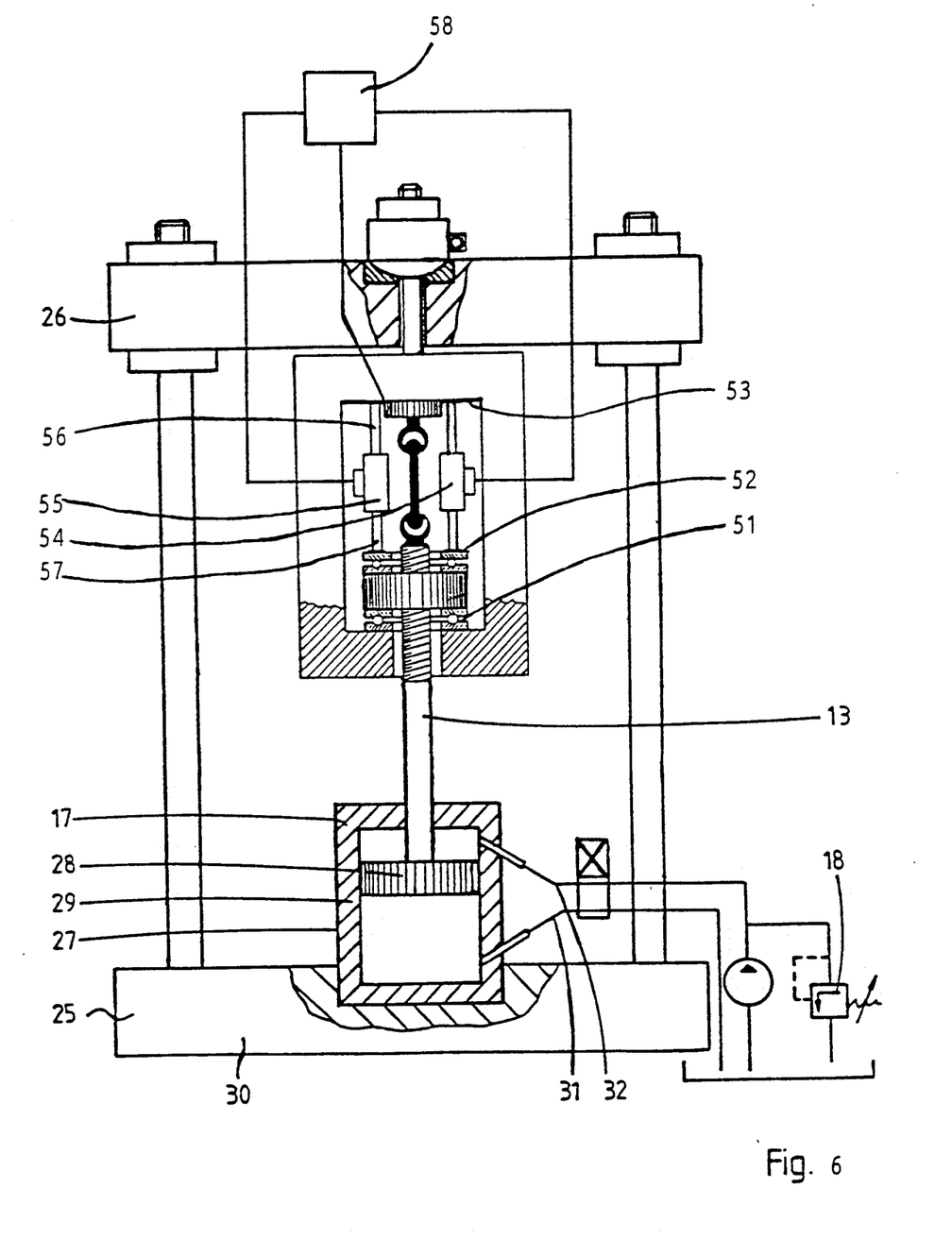
FIG. 6 a front view of a sixth embodiment of a testing machine according to the invention.

A front view of a further embodiment of the invention is shown in FIG. 6. The testing machine is essentially the same as the embodiment shown and described in FIG. 1. Only the force engagement device 11 differs from the force engagement device in FIG. 1. The setting motors 22 which reset the spindle nut 20 are not shown in this Figure for the sake of clarity.

A further axial ball bearing 51 is concentrically situated on the spindle nut 20. Two loading devices 54 and 55 which act in a vertical direction are situated between the upward facing surface area 52 of the ball bearing 51 and the downward facing surface area 53 of the upper region of the force by-pass device 11. A loading device 54 or 55 consist essentially of two hydraulic cylinders and two extendable feet 56 and 57 which are assigned to the upper or the lower surface areas 52 and 53 for force engagement. By tightening the loading device 54 or 55 loads can be symmetrically applied via the feet 56 and 57 to the upper and lower force engagement surface areas 52 and 53 of the force by-pass device 11. In addition the loading devices 54 and 55 ar fixed in the tightened state.

In order to guarantee that the actions and effect of each of the loading devices 54 and 55 are coordinated during the test these and the first force measuring device 16 are connected to control means 58 via lines. The control means 58 reacts to signals from the first force measuring device 16 in such a manner that with an increasing force applied to the sample 9 the feet 56 and 57 are increasingly pressed onto the force engagement surface areas 52 and 53 by the hydraulic cylinders of the loading devices 54 and 55. The loading and the deformation of the force by-pass device 11 is in this way kept constant during testing.

The method of testing is further optimized by the loading devices 54 and 55 according to this embodiment as even the very small relative displacements of the force by-pass device 11 can be measured in this way.

It will be understood that the above description of the present invention is susceptible to various modifications, changes and adaptations, and the same are intended to be comprehended within the meaning and range of equivalents of the appended claims.

What is claimed is:

1. Testing machine for the mechanical testing of material samples comprising
    a first and a second force engagement device,
    a first and a second sample engagement device,
    a first force measuring device positioned between said first sample engagement device and said force by-pass device together with said first force engagement device,
    an actuator for creating the force to be applied,
    a force by-pass device connected to said first force engagement device for transferring an applied prestress force acting from one of said force engagement devices to the other whilst by-passing the sample positioned between said two sample engagement devices,
    whereby
    said force by-pass device is rigid,
    said second sample engagement device being, by way of a
    length adjustment device, slideably mounted in the direction of the application of force relative to the end of said force by-pass device not being connected to one of said force engagement devices and whereby said length adjustment device is connected to said second force engagement device and said second force engagement device is connected to said actuator for creating the force to be applied whereby a device for defining the prestress force to be applied during testing is connected to said actuator.

2. Testing machine as defined in claim 1, wherein said second force measuring device is attached to one of said force engagement devices as part of said device for predetermining the prestress force to be applied.

3. Testing machine as defined in claim 1, wherein said length adjustment device comprises a spindle and a spindle nut which bears on said force by-pass device.

4. Testing machine as defined in claim 3, wherein a setting motor is attached to said force by-pass device and is connected with said spindle nut.

5. Testing machine as defined in claim 4, wherein said spindle nut and said setting motor connected thereto are attached to the inside of said force by-pass device for tensile testing.

6. Testing machine as defined in claim 4, wherein said spindle nut and said setting motor connected thereto are attached to the outside of said force by-pass device for compressive testing.

7. Testing machine as defined in claim 3, wherein said force by-pass device comprises a rectangular frame.

8. Testing machine as defined in claim 3, wherein said force by-pass device comprises a rectangular pot.

9. Testing machine as defined in claim 3, Wherein said force by-pass device comprises a rectangular cage.

10. Testing machine as defined in claim 1, wherein said length adjustment device includes a hydraulic system comprising a hydraulic cylinder and a piston; said hydraulic cylinder being connected to said second force engagement device.

11. Testing machine as defined in claim 10, wherein said hydraulic system comprises a control valve with an attached low pressure storage means, said control valve being situated near to said hydraulic cylinder.

12. Testing machine as defined in claim 1, wherein said force engagement devices are cylindrical in cross-section; said force engagement devices being fixable in the sample engagement devices of known testing machines and thereby acting as force engagement surface areas.

13. Testing machine as defined in claim 1, wherein said force engagement devices are rectangular in cross-section; said force engagement devices being fixable in the sample engagement devices of known testing machines and thereby acting as force engagement surface areas.

14. Testing machine as defined in claim 1, wherein at least one of said force engagement devices is mounted moment-free.

15. Testing machine as defined in claim 1, wherein it comprises a further loading system acting parallel to said force by-pass device; said loading system being controlled dependent on the signal from said first force measurement device and such that an additional force equivalent to the test force is applied to said force by-pass device so that the loading and the deformation of said force by-pass device remains constant during the test.

16. Testing machine as defined in claim 1, comprising a spring which stores prestress energy; said spring being mounted between said actuator and said second force engagement device.

17. Testing machine as defined in claim 1, wherein said first and second force engagement devices are moment engagement devices, said first and second force measuring devices are moment measuring devices, said actuator for creating the force to be applied is an actuator for moments, said force by-pass device is a moment by-pass device and said length adjustment device is an angle adjustment device whereby said second sample engagement device is rotatably mounted in the direction of rotation of the acting moment via said angle adjustment device on the end of said moment by-pass device which is not connected with said moment engagement device.

18. Method for the mechanical testing of material samples and parts, comprising:
(a) prestressing a testing machine using a force by-pass device and by reading a second force measuring device and applying a force which is either greater than the maximum required test force to be applied to the sample or equivalent to an applied force which is not to be exceeded during testing thereby eliminating the influence of the tractility of the testing machine completely,
(b) deforming the sample directly and definably by the controlled adjustment of a length adjustment device along a test force axis in the direction of yield in relation to the prestressing whereby the force which is applied is increasingly transferred from said force by-pass device to the sample and to said first force measuring device in accordance with the change in the resistance to deformation of the sample whilst an actuator keeps the total applied force constant and automatically resets the adjustment distance of said length adjustment device which defines the deformation path of the sample, said actuator thus providing the deformational energy required,
(c) automatically increasing the transfer of the force applied to said force by-pass device as the resistance to deformation of the sample decreases until the total force is acting on said force by-pass device by ultimate failure of the sample whereby the total force applied by said actuator remains unchanged, and
(d) unloading the testing machine after the test has finally been concluded.

19. Method as defined in claim 18, wherein the sample is subjected to changing deformations, in particular deformations changing with time in the tensile direction.

20. Method as defined in claim 18, wherein the sample is subjected to changing deformations, in particular deformations changing with time in the compressive direction.

21. Method as defined in claim 18, wherein the maximum load to be applied to the sample is predetermined by limiting the external force to be applied.

22. Method as defined in claim 18, wherein the sample is subjected to a torsional deformation in the same manner.

23. Method as defined in claim 18, wherein the sample is subjected to a plurality of torsional deformations in the same manner.

* * * * *